(12) United States Patent
Chen et al.

(10) Patent No.: US 9,950,073 B2
(45) Date of Patent: Apr. 24, 2018

(54) PEPTIDE SEQUENCE DESIGN AND USE THEREOF FOR PEPTIDE-MEDIATED SIRNA DELIVERY

(71) Applicants: Positec Power Tools (Suzhou) Co Ltd, Jiangsu Province (CN); Pu Chen, Waterloo (CA)

(72) Inventors: Pu Chen, Waterloo (CA); Mousa Jafari, Waterloo (CA); Wen Xu, Waterloo (CA); Baoling Chen, Waterloo (CA); Ran Pan, Waterloo (CA); Nedra Karunaratne, Kandy (LK)

(73) Assignees: Positec Power Tools (Suzhou) Co. Ltd., Jiangsu Province (CN); Pu Chen, Waterloo, Ontario (CA)

( * ) Notice: Subject to any disclaimer, the term of this patent is extended or adjusted under 35 U.S.C. 154(b) by 0 days.

(21) Appl. No.: 15/407,802

(22) Filed: Jan. 17, 2017

(65) Prior Publication Data
US 2017/0128582 A1 May 11, 2017

Related U.S. Application Data

(63) Continuation of application No. 14/983,194, filed on Dec. 29, 2015, now Pat. No. 9,603,946, which is a continuation of application No. 14/359,873, filed as application No. PCT/CA2012/050843 on Nov. 23, 2012, now Pat. No. 9,259,483.

(60) Provisional application No. 61/563,591, filed on Nov. 24, 2011.

(51) Int. Cl.
*A61K 47/48* (2006.01)
*C12N 15/113* (2010.01)

(52) U.S. Cl.
CPC .... *A61K 47/48246* (2013.01); *C12N 15/1135* (2013.01); *C12N 15/113* (2013.01); *C12N 2310/14* (2013.01)

(58) Field of Classification Search
CPC .......................... C12N 15/113; C12N 2310/14
See application file for complete search history.

(56) References Cited

U.S. PATENT DOCUMENTS

| | | | |
|---|---|---|---|
| 5,614,503 A | 3/1997 | Chaudhary et al. | |
| 6,514,947 B2 | 2/2003 | Rolland et al. | |
| 2007/0129305 A1 | 6/2007 | Divita et al. | |
| 2007/0281289 A1* | 12/2007 | Moon | G01N 33/533 435/4 |
| 2008/0299104 A1* | 12/2008 | Kennedy | A61K 31/7088 514/1.1 |

FOREIGN PATENT DOCUMENTS

| | | | |
|---|---|---|---|
| WO | 1996028468 | 9/1996 | |
| WO | WO 97/23607 | * 12/1996 | ........... C12N 15/113 |
| WO | 1998052614 | 11/1998 | |
| WO | 2006020121 | 2/2006 | |
| WO | 2009026729 | 3/2009 | |
| WO | 2011020188 | 2/2011 | |
| WO | 2011087804 | 7/2011 | |
| WO | 2011127210 | 10/2011 | |

OTHER PUBLICATIONS

Alshamsan et al.; "Formulation and Delivery of siRNA by Oleic Acid and Stearic Acid Modified Polyethylenimine," Molecular Pharmaceutics, (2009), vol. 6, No. 1; pp. 121-133.
Vonarbourg,et al.; "Parameters influencing the stealthiness of colloidal drug delivery systems," Biomaterials, (2006), vol. 27, pp. 4356-4373.
Biverståhl et al.; "NMR Solution Structure and Membrane Interaction of the N-Terminal Sequence (1-30) of the Bovine Prion Protein," Biochemistry, (2004), vol. 43, pp. 14940-14947.
Cartier et al.; "Utilization of synthetic peptides containing nuclear localization signals for nonviral gene transfer systems," Gene therapy, (2002), vol. 9, pp. 157-167.
Chou et al.; "Structural and Functional Role of Leucine Residues in Proteins," Journal of Molecular Biology, (1973), vol. 74, pp. 263-281.
Crombez et al.; "A New Potent Secondary Amphipathic Cell-penetrating Peptide for siRNA Delivery Into Mammalian Cells," Molecular Therapy, (2009), vol. 17, No. 1, pp. 95-103.
Knappe et al.; "Bactericidal oncocin derivatives with superior stabilities," International Journal of Antimicrobial Agents, (2011), vol. 37, pp. 166-170.
Derossi et al.; "The Third Helix of the Antennapedia Homeodomain Translocates through Biological Membranes," The Journal of Biological Chemistry, (1994), vol. 269, No. 14, Issue of Apr. 8, pp. 10444-10450.
Deshayes et al.; "Insight into the Mechanism of Internalization of the Cell-Penetrating Carrier Peptide Pep-1 through Conformational Analysis," Biochemistry, (2004), vol. 43, pp. 1449-1457.
Deshayes et al.; "Primary Amphipathic Cell-Penetrating Peptides: Structural Requirements and Interactions with Model Membranes," Biochemistry, (2004), vol. 43, pp. 7698-7706.
Endoh et al.; "Cellular siRNA delivery using cell-penetrating peptides modified for endosomal escape," Advanced Drug Delivery Reviews, (2009), vol. 61, pp. 704-709.
Engelke et al; "RNA Interference; Methods in Enzymology," Elsevier Academic Press, (2005), vol. 392, pp. 6876-6879.
Fire et al.; "Potent and specific genetic interference by double-stranded RNA in Caenorhabditis elegans," Nature, (1998), vol. 391, pp. 806-811.
Futaki et al.; "Arginine-rich Peptides. An Abundant Source of Membrane-Permeable Peptides Having Potential as Carriers for Intracellular Protein Delivery," The Journal of Biological Chemistry, (2001), vol. 276, No. 8, pp. 5836-5840.

(Continued)

*Primary Examiner* — Amy H Bowman
(74) *Attorney, Agent, or Firm* — Dunlap Codding, P.C.

(57) ABSTRACT

Peptides that have been found to facilitate the delivery of siRNA molecules into cells and to function in siRNA mediated silencing of cellular targets are disclosed. Complexes that include one of the peptides and a cargo molecule are disclosed, wherein the peptide and the cargo molecule are coupled non-covalently. Also disclosed are methods of producing and using the peptides/complexes.

18 Claims, 7 Drawing Sheets
(7 of 7 Drawing Sheet(s) Filed in Color)

(56) References Cited

OTHER PUBLICATIONS

Järver et al.; "Applications of cell-penetrating peptides in regulation of gene expression," Biochemical Society Transactions, (2007), vol. 35, part 4, pp. 770-774.
Konate et al.; "Insight into the Cellular Uptake Mechanisms of a Secondary Amphipathic Cell-Penetrating Peptide for siRNA Delivery," Biochemistry (2010), vol. 49, pp. 3393-3402.
Knappe et al; "Bactericidal oncocin derivatives with superior stabilities," International Journal of Antimicrobial Agents, (2011), vol. 37, pp. 166-170.
Langel, Ülo; "Handbook of Cell-Penetrating Peptides," 2nd Edition; CRC Press Taylor & Francis Group; Boca Raton, FL. (2007), pp. 1-624.
Mahato, Ram I.; "Biomaterials for Delivery and Targeting of Proteins and Nucleic Acids," CRC Press: Boca Raton, FL. (2005), pp. 1-681.
Lo et al.; "An endosomolytic Tat peptide produced by incorporation of histidine and cysteine residues as a nonviral vector for DNA transfection," Biomaterials, (2008), vol. 29, pp. 2408-2414.
Manoharan, Muthiah; "RNA interference and chemically modified small interfering RNAs," Elsevier Current Opinion in Chemical Biology, (2004), vol. 8, pp. 570-579.
Moghimi et al.; "Subcutaneous and intravenous delivery of diagnostic agents to the lymphatic system: applications in lymphoscintigraphy and indirect lymphography," Advanced Drug Delivery Reviews, (1999), vol. 37, pp. 295-312.
Mok et al.; "Self-Crosslinked and Reducible Fusogenic Peptides for Intracellular Delivery of siRNA," Biopolymers, (2008), vol. 89, No. 10; pp. 881-888.
Nicot et al.; "Housekeeping gene selection for real-time RT-PCR normalization in potato during biotic and abiotic stress," Journal of experimental Botany, (2005) vol. 56, No. 421, pp. 2907-2914.
Novina et al.; "The RNAi revolution," Nature, (2004), vol. 430, pp. 161-164.
Oehlke et al.; "Cellular uptake of an α-helical amphipathic model peptide with the potential to deliver polar compounds into the cell interior non-endocytically;" Biochimica et Biophysica Acta, (1998) vol. 1414, pp. 127-139.
Oliveira et al.; "Targeted Delivery of siRNA," Journal of Biomedicine and Biotechnology, vol. 2006, Article ID 63675, pp. 1-9.
Paddison et al.; "RNA interference; Current Topics in Microbiology and Immunology," (2008) vol. 320; pp. 1-274.
Tanaka et al.; "Disulfide crossliked stearoyl carrier peptides containing arginine and histidine enhance siRNA uptake and gene silencing," International Journal of Pharmaceutics, (2010) vol. 398, pp. 219-224.
Verma et al.; "Functional tuning of nucleic acids by chemical modifications: Tailored oligonucleotides as drugs, devices and diagnostics," The Chemical Record, (2003) vol. 3, No. 1, pp. 51-60.
Wadia et al.; "Pathologic Prion Protein Infects Cells by Lipid-Raft Dependent Macropinocytosis," PloS one, vol. 3, Issue 10, e3314, pp. 1-8.
Wang et al.; "Arginine-rich intracellular delivery peptides noncovalently transport protein into living cells," Biochemical and Biophysical Research Communications, (2006) vol. 346, pp. 758-767.
Zhang et al.; "RNA Interference with Chemically Modified siRNA," Current Topics in Medicinal Chemistry, (2006), vol. 6, pp. 893-900.
Vives, E. "Present and future of cell-penetrating peptide mediated delivery systems:" is the Trojan horse too wild to go only to Troy?; J Control Release, Abstract only; (2005), vol. 109, pp. 77-85.
Simeoni, et al.; "Insight into the mechanism of the peptide-based gene delivery system MPG: implications for delivery of siRNA into mammalian cells," Nucleic Acids Research, (2003) vol. 31., No. 11; pp. 2717-2724.
European Application No. 12852395.8; European Search Report dated Jun. 12, 2015.

* cited by examiner

SEQUENCE LISTING

```
<160> NUMBER OF SEQ ID NOS: 50

<210> SEQ ID NO 1
<211> LENGTH: 18
<212> TYPE: PRT
<213> ORGANISM: Artificial Sequence
<220> FEATURE:
<223> OTHER INFORMATION: C1M

<400> SEQUENCE: 1

Phe Gln Phe Asn Phe Gln Phe Asn Gly Gly Gly Pro Lys Lys Lys Arg
1               5                   10                  15

Lys Val

<210> SEQ ID NO 2
<211> LENGTH: 18
<212> TYPE: PRT
<213> ORGANISM: Artificial Sequence
<220> FEATURE:
<223> OTHER INFORMATION: C1M1

<400> SEQUENCE: 2

Phe Gln Phe Asn Phe Gln Phe Asn Gly Gly Gly Pro Lys Pro Lys Arg
1               5                   10                  15

Lys Val

<210> SEQ ID NO 3
<211> LENGTH: 22
<212> TYPE: PRT
<213> ORGANISM: Artificial Sequence
<220> FEATURE:
<223> OTHER INFORMATION: C1M2

<400> SEQUENCE: 3

Phe Gln Phe Asn Phe Gln Phe Asn Phe Gln Phe Asn Gly Gly Gly Pro
1               5                   10                  15
```

Lys Lys Lys Arg Lys Val
         20

<210> SEQ ID NO 4
<211> LENGTH: 22
<212> TYPE: PRT
<213> ORGANISM: Artificial Sequence
<220> FEATURE:
<223> OTHER INFORMATION: C1M3

<400> SEQUENCE: 4

Phe Gln Phe Asn Phe Gln Phe Asn Phe Gln Phe Asn Trp Ser Gln Pro
1               5                   10                  15

Lys Pro Lys Arg Lys Val
         20

<210> SEQ ID NO 5
<211> LENGTH: 22
<212> TYPE: PRT
<213> ORGANISM: Artificial Sequence
<220> FEATURE:
<223> OTHER INFORMATION: C1M4

<400> SEQUENCE: 5

Phe Gln Phe Asn Phe Gln Phe Asn Phe Gln Phe Asn Gly Gly Gly Pro
1               5                   10                  15

Lys Pro Lys Arg Lys Val
         20

<210> SEQ ID NO 6
<211> LENGTH: 26
<212> TYPE: PRT
<213> ORGANISM: Artificial Sequence
<220> FEATURE:
<223> OTHER INFORMATION: C1M5

<400> SEQUENCE: 6

Phe Gln Phe Asn Phe Gln Phe Asn Phe Gln Phe Asn Gly Gly Gly Cys
1               5                   10                  15

His His Arg Arg Arg Arg Arg Arg His Cys
         20                  25

<210> SEQ ID NO 7
<211> LENGTH: 24
<212> TYPE: PRT
<213> ORGANISM: Artificial Sequence
<220> FEATURE:
<223> OTHER INFORMATION: C1M6

<400> SEQUENCE: 7

Phe Gln Phe Asn Phe Gln Phe Asn Phe Gln Phe Asn Gly Gly Gly Cys
1               5                   10                  15

Pro Lys Pro Lys Arg Lys Val Cys
         20

<210> SEQ ID NO 8
<211> LENGTH: 15
<212> TYPE: PRT
<213> ORGANISM: Artificial Sequence
<220> FEATURE:
<223> OTHER INFORMATION: E3M

<400> SEQUENCE: 8

Arg Leu Thr Leu His Leu Arg Leu Glu Leu Thr Leu His Leu Glu
1               5                   10                  15

```
<210> SEQ ID NO 9
<211> LENGTH: 15
<212> TYPE: PRT
<213> ORGANISM: Artificial Sequence
<220> FEATURE:
<223> OTHER INFORMATION: E3M1

<400> SEQUENCE: 9

Arg Trp Thr Trp His Trp Arg Trp Glu Trp Thr Trp His Trp Glu
1               5                   10                  15

<210> SEQ ID NO 10
<211> LENGTH: 21
<212> TYPE: PRT
<213> ORGANISM: Artificial Sequence
<220> FEATURE:
<223> OTHER INFORMATION: A7M

<400> SEQUENCE: 10

Arg His Ala Leu Ala His Leu Leu His Lys Leu Lys His Leu Leu His
1               5                   10                  15

Ala Leu Ala His Arg
            20

<210> SEQ ID NO 11
<211> LENGTH: 21
<212> TYPE: PRT
<213> ORGANISM: Artificial Sequence
<220> FEATURE:
<223> OTHER INFORMATION: A7M1

<400> SEQUENCE: 11

Arg His Ala Leu Ala His Leu Leu His Arg Leu Arg His Leu Leu His
1               5                   10                  15

Ala Leu Ala His Arg
            20

<210> SEQ ID NO 12
<211> LENGTH: 18
<212> TYPE: PRT
<213> ORGANISM: Artificial Sequence
<220> FEATURE:
<223> OTHER INFORMATION: C6M

<400> SEQUENCE: 12

Arg Leu Trp Arg Leu Trp Leu Arg Leu Trp Arg Arg Leu Trp Arg Leu
1               5                   10                  15

Leu Arg

<210> SEQ ID NO 13
<211> LENGTH: 18
<212> TYPE: PRT
<213> ORGANISM: Artificial Sequence
<220> FEATURE:
<223> OTHER INFORMATION: C6M1

<400> SEQUENCE: 13

Arg Leu Trp Arg Leu Leu Trp Arg Leu Trp Arg Arg Leu Trp Arg Leu
1               5                   10                  15

Leu Arg

<210> SEQ ID NO 14
<211> LENGTH: 18
```

-continued

```
<212> TYPE: PRT
<213> ORGANISM: Artificial Sequence
<220> FEATURE:
<223> OTHER INFORMATION: C6M2

<400> SEQUENCE: 14

Arg Leu Trp Arg Leu Leu Trp His Leu Trp Arg His Leu Trp Arg Leu
1               5                   10                  15

Leu Arg

<210> SEQ ID NO 15
<211> LENGTH: 18
<212> TYPE: PRT
<213> ORGANISM: Artificial Sequence
<220> FEATURE:
<223> OTHER INFORMATION: C6M3

<400> SEQUENCE: 15

Arg Leu Trp His Leu Leu Trp Arg Leu Trp Arg Arg Leu His Arg Leu
1               5                   10                  15

Leu Arg

<210> SEQ ID NO 16
<211> LENGTH: 18
<212> TYPE: PRT
<213> ORGANISM: Artificial Sequence
<220> FEATURE:
<223> OTHER INFORMATION: C6M4

<400> SEQUENCE: 16

His Leu Leu Arg Leu Leu Leu Arg Leu Trp His Arg Leu Trp Arg Leu
1               5                   10                  15

Leu Arg

<210> SEQ ID NO 17
<211> LENGTH: 18
<212> TYPE: PRT
<213> ORGANISM: Artificial Sequence
<220> FEATURE:
<223> OTHER INFORMATION: C6M5

<400> SEQUENCE: 17

His Leu Trp His Leu Leu Leu Arg Leu Trp Arg Arg Leu Leu Arg Leu
1               5                   10                  15

Leu Arg

<210> SEQ ID NO 18
<211> LENGTH: 18
<212> TYPE: PRT
<213> ORGANISM: Artificial Sequence
<220> FEATURE:
<223> OTHER INFORMATION: C6M6

<400> SEQUENCE: 18

Gly Leu Trp His Leu Leu Leu His Leu Trp Arg Arg Leu Leu Arg Leu
1               5                   10                  15

Leu Arg

<210> SEQ ID NO 19
<211> LENGTH: 18
<212> TYPE: PRT
<213> ORGANISM: Artificial Sequence
<220> FEATURE:
<223> OTHER INFORMATION: C6M7
```

<400> SEQUENCE: 19

Gly Leu Trp His Leu Leu Leu His Leu Trp Arg Arg His His Arg His
1               5                   10                  15

His Arg

<210> SEQ ID NO 20
<211> LENGTH: 18
<212> TYPE: PRT
<213> ORGANISM: Artificial Sequence
<220> FEATURE:
<223> OTHER INFORMATION: C6M8

<400> SEQUENCE: 20

Gly Leu Trp His Leu His Leu His Leu Trp Arg Arg His His Arg Leu
1               5                   10                  15

Leu Arg

<210> SEQ ID NO 21
<211> LENGTH: 18
<212> TYPE: PRT
<213> ORGANISM: Artificial Sequence
<220> FEATURE:
<223> OTHER INFORMATION: C6M9

<400> SEQUENCE: 21

Gly Leu Trp His Leu Leu Leu His Leu Trp His Arg Leu Leu Arg His
1               5                   10                  15

His Arg

<210> SEQ ID NO 22
<211> LENGTH: 24
<212> TYPE: PRT
<213> ORGANISM: Artificial Sequence
<220> FEATURE:
<223> OTHER INFORMATION: MW1

<400> SEQUENCE: 22

Met Trp Lys Ser Lys Ile Gly Ser Trp Ile Leu Val Arg Trp Ala Met
1               5                   10                  15

Trp Ser Lys Lys Arg Pro Lys Pro
            20

<210> SEQ ID NO 23
<211> LENGTH: 24
<212> TYPE: PRT
<213> ORGANISM: Artificial Sequence
<220> FEATURE:
<223> OTHER INFORMATION: MW2

<400> SEQUENCE: 23

Met Trp Lys Ser His Ile Gly Ser Trp Ile Leu Val Arg Trp Ala Met
1               5                   10                  15

Trp Ser His Lys Arg Pro Lys Pro
            20

<210> SEQ ID NO 24
<211> LENGTH: 23
<212> TYPE: PRT
<213> ORGANISM: Artificial Sequence
<220> FEATURE:
<223> OTHER INFORMATION: MW3

<400> SEQUENCE: 24

-continued

Met Trp Lys Ser Lys Ile Ser Trp Ile Leu Val Ser Lys Pro Gly Leu
1               5                   10                  15

Cys Lys Lys Arg Pro Lys Pro
            20

<210> SEQ ID NO 25
<211> LENGTH: 23
<212> TYPE: PRT
<213> ORGANISM: Artificial Sequence
<220> FEATURE:
<223> OTHER INFORMATION: MW4

<400> SEQUENCE: 25

Met His Lys Ser Lys Ile Ser Trp His Leu Val Ser Lys Pro Gly Leu
1               5                   10                  15

Cys His Lys Arg Pro Lys Pro
            20

<210> SEQ ID NO 26
<211> LENGTH: 18
<212> TYPE: PRT
<213> ORGANISM: Artificial Sequence
<220> FEATURE:
<223> OTHER INFORMATION: C6-Dr

<400> SEQUENCE: 26

Arg Leu Leu Arg Leu Leu Leu Arg Leu Trp Arg Arg Leu Leu Arg Leu
1               5                   10                  15

Leu Arg

<210> SEQ ID NO 27
<211> LENGTH: 18
<212> TYPE: PRT
<213> ORGANISM: Artificial Sequence
<220> FEATURE:
<223> OTHER INFORMATION: C6-D

<400> SEQUENCE: 27

Arg Leu Leu Arg Leu Leu Leu Arg Leu Trp Arg Arg Leu Leu Arg Leu
1               5                   10                  15

Leu Arg

<210> SEQ ID NO 28
<211> LENGTH: 18
<212> TYPE: PRT
<213> ORGANISM: Artificial Sequence
<220> FEATURE:
<223> OTHER INFORMATION: C6M1-Dr

<400> SEQUENCE: 28

Arg Leu Trp Arg Leu Leu Trp Arg Leu Trp Arg Arg Leu Trp Arg Leu
1               5                   10                  15

Leu Arg

<210> SEQ ID NO 29
<211> LENGTH: 18
<212> TYPE: PRT
<213> ORGANISM: Artificial Sequence
<220> FEATURE:
<223> OTHER INFORMATION: C6M1-D

<400> SEQUENCE: 29

Arg Leu Trp Arg Leu Leu Trp Arg Leu Trp Arg Arg Leu Trp Arg Leu

-continued

```
1               5                   10                  15

Leu Arg

<210> SEQ ID NO 30
<211> LENGTH: 18
<212> TYPE: PRT
<213> ORGANISM: Artificial Sequence
<220> FEATURE:
<223> OTHER INFORMATION: C6M3-Dr

<400> SEQUENCE: 30

Arg Leu Trp His Leu Leu Trp Arg Leu Trp Arg Arg Leu His Arg Leu
1               5                   10                  15

Leu Arg

<210> SEQ ID NO 31
<211> LENGTH: 18
<212> TYPE: PRT
<213> ORGANISM: Artificial Sequence
<220> FEATURE:
<223> OTHER INFORMATION: C6M3-D

<400> SEQUENCE: 31

Arg Leu Trp His Leu Leu Trp Arg Leu Trp Arg Arg Leu His Arg Leu
1               5                   10                  15

Leu Arg

<210> SEQ ID NO 32
<211> LENGTH: 18
<212> TYPE: PRT
<213> ORGANISM: Artificial Sequence
<220> FEATURE:
<223> OTHER INFORMATION: C6M6-Dr

<400> SEQUENCE: 32

Gly Leu Trp His Leu Leu Leu His Leu Trp Arg Arg Leu Leu Arg Leu
1               5                   10                  15

Leu Arg

<210> SEQ ID NO 33
<211> LENGTH: 18
<212> TYPE: PRT
<213> ORGANISM: Artificial Sequence
<220> FEATURE:
<223> OTHER INFORMATION: C6M6-D

<400> SEQUENCE: 33

Gly Leu Trp His Leu Leu Leu His Leu Trp Arg Arg Leu Leu Arg Leu
1               5                   10                  15

Leu Arg

<210> SEQ ID NO 34
<211> LENGTH: 24
<212> TYPE: PRT
<213> ORGANISM: Artificial Sequence
<220> FEATURE:
<223> OTHER INFORMATION: GL1

<400> SEQUENCE: 34

Gly Leu Trp Arg Ala Trp Leu Trp Lys Ala Phe Leu Ala Ser Asn Trp
1               5                   10                  15

Arg Arg Leu Leu Arg Leu Leu Arg
            20
```

<210> SEQ ID NO 35
<211> LENGTH: 24
<212> TYPE: PRT
<213> ORGANISM: Artificial Sequence
<220> FEATURE:
<223> OTHER INFORMATION: GL2

<400> SEQUENCE: 35

Gly Leu Trp Arg Ala Ser Trp Leu Lys Ala Trp Leu Ala Ser Asn Trp
1               5                   10                  15

His Lys Lys His Arg Leu Leu Arg
            20

<210> SEQ ID NO 36
<211> LENGTH: 25
<212> TYPE: PRT
<213> ORGANISM: Artificial Sequence
<220> FEATURE:
<223> OTHER INFORMATION: GL3

<400> SEQUENCE: 36

Gly Leu Trp Gly Ala Trp Phe Ile Glu Gly Trp Glu Gly Met Ile Asp
1               5                   10                  15

Gly Arg Arg Leu Leu Arg Leu Leu Arg
            20                  25

<210> SEQ ID NO 37
<211> LENGTH: 23
<212> TYPE: PRT
<213> ORGANISM: Artificial Sequence
<220> FEATURE:
<223> OTHER INFORMATION: GL4

<400> SEQUENCE: 37

Gly Leu Trp Arg Ala Ser Trp Leu Lys Ala Phe Leu Ala Ser Asn Trp
1               5                   10                  15

His Lys Lys Leu His Lys Lys
            20

<210> SEQ ID NO 38
<211> LENGTH: 38
<212> TYPE: PRT
<213> ORGANISM: Artificial Sequence
<220> FEATURE:
<223> OTHER INFORMATION: HA2-C6

<400> SEQUENCE: 38

Gly Leu Phe Gly Ala Ile Ala Gly Phe Ile Glu Asn Gly Trp Glu Gly
1               5                   10                  15

Met Ile Asp Gly Arg Leu Leu Arg Leu Leu Arg Leu Trp Arg Arg
            20                  25                  30

Leu Leu Arg Leu Leu Arg
        35

<210> SEQ ID NO 39
<211> LENGTH: 30
<212> TYPE: PRT
<213> ORGANISM: Artificial Sequence
<220> FEATURE:
<223> OTHER INFORMATION: HA2-PK

<400> SEQUENCE: 39

Gly Leu Phe Gly Ala Ile Ala Gly Phe Ile Glu Asn Gly Trp Glu Gly

```
                1               5                  10                 15
Met Ile Asp Gly Trp Tyr Gly Pro Lys Lys Arg Lys Val
            20                  25                 30

<210> SEQ ID NO 40
<211> LENGTH: 10
<212> TYPE: PRT
<213> ORGANISM: Artificial Sequence
<220> FEATURE:
<223> OTHER INFORMATION: STR-C1
<220> FEATURE:
<221> NAME/KEY: MISC_FEATURE
<222> LOCATION: (1)..(1)
<223> OTHER INFORMATION: STR modified sequence

<400> SEQUENCE: 40

Gly Gly Gly Pro Lys Pro Lys Arg Lys Val
1               5                  10

<210> SEQ ID NO 41
<211> LENGTH: 10
<212> TYPE: PRT
<213> ORGANISM: Artificial Sequence
<220> FEATURE:
<223> OTHER INFORMATION: STR-HK
<220> FEATURE:
<221> NAME/KEY: MISC_FEATURE
<222> LOCATION: (1)..(1)
<223> OTHER INFORMATION: STR modified sequence

<400> SEQUENCE: 41

His His His Pro Lys Pro Lys Arg Lys Val
1               5                  10

<210> SEQ ID NO 42
<211> LENGTH: 12
<212> TYPE: PRT
<213> ORGANISM: Artificial Sequence
<220> FEATURE:
<223> OTHER INFORMATION: STR-HKC
<220> FEATURE:
<221> NAME/KEY: MISC_FEATURE
<222> LOCATION: (1)..(1)
<223> OTHER INFORMATION: STR modified sequence

<400> SEQUENCE: 42

His His His Cys Pro Lys Lys Lys Arg Lys Val Cys
1               5                  10

<210> SEQ ID NO 43
<211> LENGTH: 18
<212> TYPE: PRT
<213> ORGANISM: Artificial Sequence
<220> FEATURE:
<223> OTHER INFORMATION: C6-CYSt
<220> FEATURE:
<221> NAME/KEY: MISC_FEATURE
<222> LOCATION: (18)..(18)
<223> OTHER INFORMATION: CYSt modified sequence

<400> SEQUENCE: 43

Arg Leu Leu Arg Leu Leu Leu Arg Leu Trp Arg Arg Leu Leu Arg Leu
1               5                  10                 15

Leu Arg

<210> SEQ ID NO 44
<211> LENGTH: 18
<212> TYPE: PRT
```

```
<213> ORGANISM: Artificial Sequence
<220> FEATURE:
<223> OTHER INFORMATION: C6M1-CYSt
<220> FEATURE:
<221> NAME/KEY: MISC_FEATURE
<222> LOCATION: (18)..(18)
<223> OTHER INFORMATION: CYSt modified sequence

<400> SEQUENCE: 44

Arg Leu Trp Arg Leu Leu Trp Arg Leu Trp Arg Arg Leu Trp Arg Leu
1               5                   10                  15

Leu Arg

<210> SEQ ID NO 45
<211> LENGTH: 18
<212> TYPE: PRT
<213> ORGANISM: Artificial Sequence
<220> FEATURE:
<223> OTHER INFORMATION: C6M3-CYSt
<220> FEATURE:
<221> NAME/KEY: MISC_FEATURE
<222> LOCATION: (18)..(18)
<223> OTHER INFORMATION: CYSt modified sequence

<400> SEQUENCE: 45

Arg Leu Trp His Leu Leu Trp Arg Leu Trp Arg Arg Leu His Arg Leu
1               5                   10                  15

Leu Arg

<210> SEQ ID NO 46
<211> LENGTH: 18
<212> TYPE: PRT
<213> ORGANISM: Artificial Sequence
<220> FEATURE:
<223> OTHER INFORMATION: C6M6-CYSt
<220> FEATURE:
<221> NAME/KEY: MISC_FEATURE
<222> LOCATION: (18)..(18)
<223> OTHER INFORMATION: CYSt modified sequence

<400> SEQUENCE: 46

Gly Leu Trp His Leu Leu Leu His Leu Trp Arg Arg Leu Leu Arg Leu
1               5                   10                  15

Leu Arg

<210> SEQ ID NO 47
<211> LENGTH: 21
<212> TYPE: DNA
<213> ORGANISM: Artificial Sequence
<220> FEATURE:
<223> OTHER INFORMATION: Primer 1

<400> SEQUENCE: 47
ttgctgttga agtcgcagga g                                         21

<210> SEQ ID NO 48
<211> LENGTH: 20
<212> TYPE: DNA
<213> ORGANISM: Artificial Sequence
<220> FEATURE:
<223> OTHER INFORMATION: Primer 2

<400> SEQUENCE: 48
tgtgtccgtc gtggatctga                                           20

<210> SEQ ID NO 49
```

```
<211> LENGTH: 24
<212> TYPE: DNA
<213> ORGANISM: Artificial Sequence
<220> FEATURE:
<223> OTHER INFORMATION: Primer 3

<400> SEQUENCE: 49
agggtttctc cacttcgatc ttgc                                          24

<210> SEQ ID NO 50
<211> LENGTH: 24
<212> TYPE: DNA
<213> ORGANISM: Artificial Sequence
<220> FEATURE:
<223> OTHER INFORMATION: Primer 4

<400> SEQUENCE: 50
agatggcaca ggaggaaaga gcat                                          24
```

PEPTIDE SEQUENCE DESIGN AND USE THEREOF FOR PEPTIDE-MEDIATED SIRNA DELIVERY

CROSS REFERENCE TO RELATED APPLICATIONS/INCORPORATION BY REFERENCE STATEMENT

This application is a continuation of U.S. Ser. No. 14/983,194, filed Dec. 29, 2015; which is a continuation of U.S. Ser. No. 14/359,873, filed May 21, 2014, now U.S. Pat. No. 9,259,483, issued Feb. 16, 2016; which is a 35 USC § 371 national stage application of PCT Application No. PCT/CA2012/050843, filed Nov. 23, 2012; which claims priority under the Paris Convention to U.S. Application No. 61/563,591, filed on Nov. 24, 2011. The entire contents of the above-referenced applications are expressly incorporated herein by reference.

TECHNICAL FIELD

The presently disclosed and/or claimed inventive concept(s) relates to peptide sequences and their use for short interfering RNA (siRNA) delivery.

BACKGROUND

Over the past decade, we have witnessed tremendous progress in our understanding of the role of RNA molecules in the regulation of gene expression. The main contribution to this progress was offered by the discovery of RNA interference (RNAi). First identified in *C. elegans* by Fire and Mello [Fire, et al. 1998], RNAi is an evolutionary conserved mechanism that brings about a sequence specific, post transcriptional gene silencing (PTGS) through the use of short RNAs. The basic idea behind RNAi is that a short RNA duplex of 21-23 nucleotides, termed short interfering RNA or siRNA, complementary to a segment of the mRNA, can be exogenously synthesized and introduced into the cell. This triggers a process which finally degrades the homologous mRNA and inhibits the production of the corresponding protein. Several types of short RNAs, including short interfering RNA (siRNA), micro RNA (miRNA), tiny non-coding RNA (tncRNA), and short hairpin RNA (shRNA), may be involved in RNAi process [Novina, et al. 2004, Paddison, et al. 2008, Engelke, et al. 2005].

The major limitations for the use of siRNA both in vitro and in vivo are the instability of naked siRNA in physiological conditions, rapid clearance from the bloodstream, and the inability to cross the cellular membrane to gain access to the intracellular environment. Because of their small size and hydrophilicity, a significant portion of administrated naked siRNAs are excreted through the reticuloendothelial system (RES) [Moghimi, et al. 1999]. It was also reported that highly charged particles can be recognized by the RES more rapidly than neutral or slightly charged particles [Benoit, et al. 2006, Mahato. 2005]. Furthermore, nucleic acid (NA)-based drugs are subjected to enzymatic degradation during circulation and within the cell, resulting in insufficient drug potency at the target site. Chemical modifications in the sugars, nucleobases, and the phosphate ester backbone of siRNA have been applied to improve its nuclease resistance without interfering with the silencing efficiency [Manoharan 2004, Verma, et al. 2003, Zhang, et al. 2006]. Conjugation with hydrophobic functional groups has also enhanced the cellular uptake [Oliviera et al., 2006].

In comparison with chemical modifications of NAs, which is time-consuming and costly, carrier-mediated strategies are emerging as a simple and fast means to formulate NA therapeutics and protect them from degradation. The carriers, including viral vectors, lipids, polymers, and peptides, co-assembled or covalently conjugated with siRNA, are designed to enhance cell targeting, prolong drug circulation time, and improve membrane permeation.

Because of their diversity and versatility in design, through the use of amino acids with different physicochemical properties, peptides have been employed to deliver synthetic drugs, small molecules, bioactive peptides, therapeutic proteins, and NAs by a mechanism that has not yet been fully understood. These peptides may include protein-derived cell penetrating peptides (CPPs) [Langel 2007], cationic peptides [Benoit, et al. 2006], designed amphiphilic peptides [Oehlke, et al. 1998], fusogenic peptides [Mok, et al. 2008], cell targeting peptides (CTP) [vives 2005], and peptides containing a nuclear localization signal [Cartier, et al. 2002]. Cationic peptides rich in basic amino acids can electrostatically interact with small NAs or condense NA into small stable particles. CPPs can facilitate the translocation of the complex through the cell membrane. Histidine-rich pH-sensitive or fusogenic peptides can enhance the endosomal escape and cytoplasmic release of the gene complex. Involvement of CTPs in gene delivery systems mediates cell and/or tissue-specific targeting. Finally, attachment of a NLS peptide improves nuclear localization of the gene complex.

Among CPPs, only few have shown high transfection efficiency with low cytotoxicity and immunogenicity. Tat and Penetratin are the most widely investigated peptides among protein-derived peptides. Trans-activating transcriptional activator (Tat) from Human Immunodeficiency Virus 1 (HIV-1), discovered by Frankel and Pabo in 1988, can be efficiently taken up by several cell types in culture [Jarvert, et al. 2007].

Specific cell-penetrating peptides (CPPs) identified as effective carriers for NAs have been described, see e.g. International Patent Application Publication Nos. WO 2007/076904 to Brock et al. and WO 2007/069090 to Divita et al., although not all describe the transport of siRNA, see e.g. U.S. Pat. No. 7,163,695 to Mixson and U.S. Pat. No. 7,112,442 to Rice et al.

In many of these carrier-mediated delivery systems the NA is covalently linked to a carrier peptide of a specific sequence, see e.g. International Patent Application Publication No. WO 2008/063113 to Langel et al. and United States Patent Application Publication No. US 2005/0260756 to Troy et al. Specific peptides have been linked to NA via chemical linkers, see e.g. WO 2008/033285 to Troy et al and WO 2007/069068 to Alluis et al. U.S. Pat. No. 7,420,031 to Karas reports a peptide capable of delivering NAs to an intracellular compartment of a cell; the peptide-cargo moiety complex is formed by a chemical cross-linking or bridging method. U.S. Pat. No. 7,306,784 to Piwinica-Worms describes use of cell membrane-permeant peptide conjugate coordination and covalent complexes having target cell specificity.

United States Patent Application Publication No. US 2008/0234183 to Hallbrink et al. describes methods for predicting, designing, detecting and verifying CPPs. The CPP-cargo complexes of Hallbrink et al. involve a covalent linkage between the CPP and cargo molecule.

International Patent Application Publication No. WO 2010/039088 to Kariem et al. describes the use of some stearylated linear or branched CPPs, in particular Transportan and Penetratin, in NA delivery.

U.S. Pat. No. 6,800,481 to Holmes et al. describes the self-assembly of amphiphilic peptides, i.e., peptides with alternating hydrophobic and hydrophilic residues, into macroscopic membranes.

International Patent Application Publication No. WO 2003/106491 to Langel et al. describes methods for predicting, designing, detecting, and verifying CPPs and their use for improved cellular uptake of a cellular effector coupled to the CPP.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIGS. 3A and 3B show two different runs.

FIG. 4A shows 18 peptide-siRNA complexes. FIG. 4B shows 6 peptide-siRNA complexes.

FIG. 8A shows photographs of tumor tissue where mice were killed by cervical dislocation before tumors were separated. FIG. 8B shows antitumor activity of siRNA/C6M1 complex in a mouse tumor model; wherein the complexes were administered intra-tumorly in mice model bearing A549 cancer cells xenografted under the skin and tumor sizes were measured everyday. FIG. 8C shows body weights of the mice, measured everyday during treatment.

DETAILED DESCRIPTION

Figure 1:
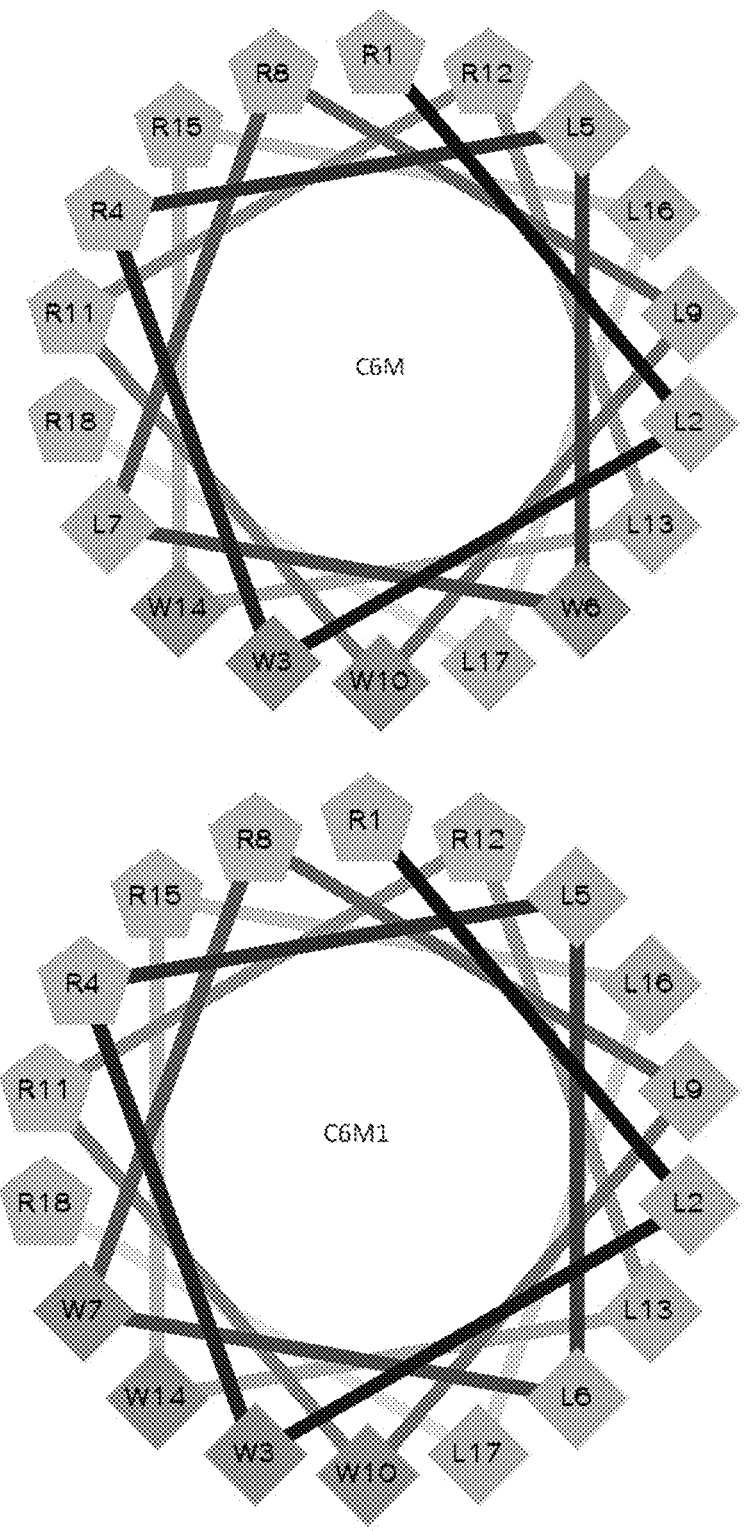
FIG. 1 illustrates the helical wheel projections of C6M and C6M1 peptides.

The peptide-cargo complexes of the presently disclosed and/or claimed inventive concept(s) are formed by a noncovalent molecular association through weak interactions between peptide and siRNA, which provides a simple and fast means to formulate siRNA therapeutics.

The molecular association of the complexes of the presently disclosed and/or claimed inventive concept(s) is less expensive and complex than cross-linking or bridging methods. Through this assembly, peptide-siRNA complexes/assemblies, often in the form of nanoparticles, can be conveniently generated.

Considering the amphiphilic nature of the cell membrane, certain designed peptides possess both hydrophilic and hydrophobic moieties. The hydrophilic side interacts with hydrophilic drugs/genes, and the hydrophilic heads of the lipid bilayer through electrostatic interaction, while the hydrophobic side is anchored in the hydrophobic core of the bilayer, assisting the translocation of peptide-cargo to the cytosol.

In one embodiment, there is provided a peptide having the amino acid sequence selected from SEQ. ID. NO 1 to SEQ. ID. NO 46.

In another embodiment, the presently disclosed and/or claimed inventive concept(s) provides a complex of a peptide and a cargo molecule, wherein the peptide has the amino acid sequence selected from SEQ. ID. NO 1 to SEQ. ID. NO 46.

In a certain, non-limiting embodiment, the cargo molecules of the presently disclosed and/or claimed inventive concept(s) are NAs and, in a particular, non-limiting embodiment, the cargo is siRNA.

In another embodiment, there is provided a pharmaceutical composition of the complex for delivering a therapeutically effective amount of siRNA.

In another embodiment, there is provided a method for reducing the levels of a gene product within a cell or tissue of an animal comprising administering a therapeutically effective amount of siRNA.

In another embodiment, there is provided a method for reducing the levels of a gene product that regulates apoptosis.

I. C1 Peptides:

In one embodiment, the presently disclosed and/or claimed inventive concept(s) provides peptides having the following amino acid sequences:

TABLE 1

C1 family peptide sequences

| Name | Sequence | SEQ ID NO: |
|------|----------|------------|
| C1M  | FQFNFQFNGGGPKKKRKV | (SEQ ID NO: 1) |
| C1M1 | FQFNFQFNGGGPKPKRKV | (SEQ ID NO: 2) |
| C1M2 | FQFNFQFNFQFNGGGPKKKRKV | (SEQ ID NO: 3) |
| C1M3 | FQFNFQFNFQFNWSQPKPKRKV | (SEQ ID NO: 4) |
| C1M4 | FQFNFQFNFQFNGGGPKPKRKV | (SEQ ID NO: 5) |
| C1M5 | FQFNFQFNFQFNGGGCHHRRRRRRHC | (SEQ ID NO: 6) |
| C1M6 | FQFNFQFNFQFNGGGCPKPKRKVC | (SEQ ID NO: 7) |

This group of peptides was designed to explore the possibility of using peptides with β-strand secondary structures as delivery vehicles. The hydrophobic and hydrophilic segments at two opposite ends of these sequences are joined through a linker. In International Patent Application Publication No. WO 2009/026729, Chen et al. describe different mechanisms including electrostatic, hydrogen bonding, hydrophobic, and π-π stacking interactions incorporated in peptide assembly. These strategies were applied in designing the hydrophobic section of this class of peptides which can self assemble through complementarity of weak interaction such as hydrogen bonding and hydrophobic forces. The length of hydrophobic section has also changed in C1M2 to C1M4 from 8 to 12 amino acids, to evaluate the significance of hydrophobic segment length.

The linker, GGG, was used to link the hydrophobic and hydrophilic together while keeping the flexibility in the peptide backbone. The linker was changed in C1M3 to WSQP to evaluate any possible effect of linker [Deshayes, et al. 2004].

The positively-charged hydrophilic segment is responsible for both co-assembling with siRNA and approaching the cell membrane through electrostatic interaction between guanidino groups in arginine and lysine of the peptide and phosphate groups in siRNA backbone and phospholipid bilayers of the cells. A nuclear localization sequence (NLS), PKKKRKV, in C1M replaced the arginine-rich segment of peptide C1, with a sequence of FQFNFQF-NGGGHRRRRRRR, originally reported in International Patent Application Publication No. WO 2011/020188 to Chen et al. (the entire disclosure of which is incorporated herein by reference). The sequence was further modified by a single mutation of a lysine residue in NLS to a proline residue in order to limit its nuclear translocation and rapid release of the cargo in the cytoplasm in C1M1, C1M3, and C1M4. The hydrophilic segment was also replaced with CHHRRRRRRHC and CPKPKRKVC in C1M5 and C1M6, respectively, to evaluate the effect of cystine amino acid in enhancing the release of siRNA from the complex due to the pH change in endosome and cytoplasm.

II. E3 Peptides:

In another embodiment, the presently disclosed and/or claimed inventive concept(s) provides peptides having the following amino acid sequences:

TABLE 2

E3 family peptide sequences

| Name | Sequence | SEQ ID NO: |
|---|---|---|
| E3M | RLTLHLRLELTLHLE | (SEQ ID NO: 8) |
| E3M1 | RWTWHWRWEWTWHWE | (SEQ ID NO: 9) |

This group of peptides was also designed based on amino acid paring strategies mentioned by Chen et al. in International Patent Application Publication No. WO 2009/026729. However, in this class of peptides, unlike C1 family peptides, the hydrophilic amino acids, R and H, are distributed among the hydrophobic residues. The peptide E3, with a sequence of RFTFHFRFEFTFHFE, was originally reported in International Patent Application Publication No. WO 2011/020188 by Chen et al. Here, we have further modified this sequence. The self-assembly of these sequences is favored by electrostatic interaction between R and E, hydrogen bonding between T and H, and hydrophobic interaction between F's in E3, L's in E3M, and W's in E3M1. The histidine residues were also used to enhance the endosomal escape for the complex as it is protonated at low pH. When a histidine containing peptide is taken into the endosome during endocytosis, it may act as a proton sponge, disrupting the endosomal pH balance, releasing the complex from the endosome. The hydrophobic amino acids, L and W in E3M and E3M1, respectively, replaced F residues in E3 to evaluate the effect of hydrophobic strength of peptides. Furthermore, tryptophan residues were reported to facilitate translocation of the peptide through the cell membrane.

III. A7 Peptides:

In another embodiment, the presently disclosed and/or claimed inventive concept(s) provides peptides having the following amino acid sequences:

TABLE 3

A7 family peptide sequences

| A7M | RHALAHLLHKLKHLLHALAHR | (SEQ ID NO: 10) |
|---|---|---|
| A7M1 | RHALAHLLHRLRHLLHALAHR | (SEQ ID NO: 11) |

The group, mainly consisted of arginine, lysine, histidine, leucine, and alanine, was designed to have an α-helical secondary structure having three distinct sections when viewed from the top, each contributed by the amino acids leucine and/or alanine, arginine and/or lysine, and histidine. It is believed that hydrophobic residues such as leucine may assist in cell penetration through interacting with the hydrophobic tails in the lipid bilayer of the cell, and also assist in pore formation in the cell membrane [Langel 2007]. Several studies have investigated the translocation efficiency of arginine-rich peptides of various lengths. It was found that peptides with seven to nine arginine residues have the highest translocation efficiency, while at least five arginine/lysine residues are required for translocation to take place. Histidine, as mentioned above, is a pH sensitive amino acid as it will be protonated at low pH. When a histidine containing peptide is taken into the endosome during endocytosis, it may act as a proton sponge, disrupting the endosomal pH balance. This may result in the leakage of the endosomal content, releasing the siRNA complexes to the cytosol. Peptide A7, with a sequence of HRLRHALAHL-LHKLKHLLHALAHRLRH, originally reported in International Patent Application Publication No. WO 2011/020188 by Chen et al. Here, we evaluated the sequence length effect, as well as the effect of replacement of arginine with lysine in A7M and A7M1.

IV. C6 Peptides:

In another embodiment, the presently disclosed and/or claimed inventive concept(s) provides peptides having the following amino acid sequences:

TABLE 4

C6 family peptide sequences

| Name | Sequence | SEQ ID NO: |
|---|---|---|
| C6M | RLWRLWLRLWRRLWRLLR | (SEQ ID NO: 12) |
| C6M1 | RLWRLLWRLWRRRLWRLLR | (SEQ ID NO: 13) |
| C6M2 | RLWRLLWHLWRHLWRLLR | (SEQ ID NO: 14) |
| C6M3 | RLWHLLWRLWRRLHRLLR | (SEQ ID NO: 15) |
| C6M4 | HLLRLLLRLWHRLWRLLR | (SEQ ID NO: 16) |
| C6M5 | HLWHLLLRLWRRLLRLLR | (SEQ ID NO: 17) |
| C6M6 | GLWHLLLHLWRRLLRLLR | (SEQ ID NO: 18) |
| C6M7 | GLWHLLLHLWRRHHRHHR | (SEQ ID NO: 19) |
| C6M8 | GLWHLHLHLWRRHHRLLR | (SEQ ID NO: 20) |
| C6M9 | GLWHLLLHLWHRLLRHHR | (SEQ ID NO: 21) |

This group of peptides was designed based on peptide C6, reported by Chen et al, in International Patent Application Publication No. WO 2009/026729 (the entire disclosure of which is incorporated herein by reference). C6 was designed to contain seven positively charged arginine residues. Arginine rich peptides are reported to be capable of delivering siRNA into cells with high efficiency and low toxicity

[Futaki, et al., 2001; Wang, et al., 2006] while at least five arginine residues are required to maintain the transfection efficiency. Hydrophobic residues such as leucine are also included in C6 sequence. These hydrophobic amino acids can facilitate the translocation of peptide by interacting with the hydrophobic tails in the lipid bilayer or assisting in pore formation in the cell membrane [Langel. 2007]. It has been found that alanine, leucine and histidine are found abundantly in the helical regions of proteins [Chou and Fasman 1973]. They indicate that leucine is the strongest structure forming residue in the proteins they investigated.

C6 sequence was modified to increase its solubility and transfection efficiency, and series of derivatives were obtained. The derivatives were designed to allow positioning of hydrophilic and hydrophobic residues on opposite faces of the molecule, upon adapting a helical structure. FIG. 1 shows the amino acids have been predicted to position the nonpolar and polar amino acids in the two different faces of the helix, possibly to facilitate self/co assembly. Some hydrophobic leucine residues are selectively substituted with less hydrophobic tryptophan residues to improve their solubility in water. Meanwhile, the aromatic tryptophan is reported to play an essential role in the cellular uptake of many cell-penetrating peptides [Derossi, et al. 1994; Heitz, et al. 2004], as they are able to interact with the lipid/cholesterol within the cell membrane. Histidine is a pH sensitive amino acid, suitable to be contained in a peptide sequence exhibiting the ability to interact with siRNA molecules and to favor the escape of siRNA from endosomes, due to the protonation effect of its imidazole ring at pH 6 [Lo & S. Wang, 2008]. This results in the leakage of the endosomal content, releasing siRNA into the cytoplasm where RNA interference happens. Tryptophan and histidine, were added at different positions in the peptide sequence to combine their cell penetration and endosomal disruption capabilities. The C6 derivatives incorporate functional moieties of various co-assembling peptides, cell penetrating peptides and endosomal disruptive peptides.

V. MW Peptides:

In another embodiment, the presently disclosed and/or claimed inventive concept(s) provides peptides having the following amino acid sequences:

TABLE 5

MW family peptide sequences

| Name | Sequence | SEQ ID NO: |
|------|----------|------------|
| MW1 | MWKSKIGSWILVRWAMWSKKRPKP | (SEQ ID NO: 22) |
| MW2 | MWKSHIGSWILVRWAMWSHKRPKP | (SEQ ID NO: 23) |
| MW3 | MWKSKISWILVSKPGLCKKRPKP | (SEQ ID NO: 24) |
| MW4 | MHKSKISWHLVSKPGLCHKRPKP | (SEQ ID NO: 25) |

This group of peptides is derived from N-terminal sequence (1-30) of the bovine prion protein (bPrPp). The bovine PrP with the sequence of MVKSKIGSWILVLF-VAMWSDV GLCKKRPKP adopts a largely a-helical structure [Biverståhl, et al. 2004]. The basic sequence of bovine PrP (residues 23-28) resembles a nuclear localization sequence (NLS) and stimulates cellular uptake by lipid raft-dependent and macropinocytosis [Wadia, et al. 2008]. The transfection efficiency of Bovine PrP is reported to be 48% [Endoh & Ohtsuki, 2009]. Thus, some trypotophan and histidine residues are added to the sequence to increase the affinity of the peptide with membrane and promote endosomal escape.

VI. D-Form Peptides:

In another embodiment, the presently disclosed and/or claimed inventive concept(s) provides peptides having the following amino acid sequences:

TABLE 6

D-form peptidesequences

| Name | Sequences | SEQ ID NO: |
|------|-----------|------------|
| C6-Dr | rLLrLLLrLWrrLLrLLr | (SEQ ID NO: 26) |
| C6-D | rllrlllrlwrrllrllr | (SEQ ID NO: 27) |
| C6M1-Dr | rLWrLLWrLWrrLWrLLr | (SEQ ID NO: 28) |
| C6M1-D | rlwrllwrlwrrlwrllr | (SEQ ID NO: 29) |
| C6M3-Dr | rLWHLLWrLWrrLHrLLr | (SEQ ID NO: 30) |
| C6M3-D | rlwhllwrlwrrlhrllr | (SEQ ID NO: 31) |
| C6M6-Dr | GLWHLLLHLWrrLLrLLr | (SEQ ID NO: 32) |
| C6M6-D | glwhlllhlwrrllrllr | (SEQ ID NO: 33) |

For the peptide mediated drug delivery system, the peptide is not only responsible for the delivery of siRNA, but also plays an important role in protecting siRNA from the degradation by nucleases in serum, which will influence the gene silencing efficiency. This gives us the hint to make modifications of some peptide sequences.

One of the obstacles in transfection is the cell membrane. It has been reported that D-form of R(r) could enhance the cell penetration ability and enhance the serum stability. The L-form of R was replaced with the D-form of R(r) in sequences of C6, C6M1, C6M3 and C6M6.

Using the D-form of R(r) also affects the secondary structure of the peptide, and correspondingly may influence the shape and size of the peptide-siRNA complex. Peptide sequences C6, C6M1, C6M3 and C6M6 were converted into total D-form to alter transfection efficiency, stability, and cytotoxicity.

VII. GL Peptides:

In another embodiment, the presently disclosed and/or claimed inventive concept(s) provides peptides having the following amino acid sequences:

TABLE 7

GL peptide sequences

| Name | Sequence | SEQ ID NO: |
|------|----------|------------|
| GL1 | GLWRAWLWKAFLASNWRRLLRLLR | (SEQ ID NO: 34) |
| GL2 | GLWRASWLKAWLASNWHKKHRLLR | (SEQ ID NO: 35) |
| GL3 | GLWGAWFIEGWEGMIDGRRLLRLLR | (SEQ ID NO: 36) |
| GL4 | GLWRASWLKAFLASNWHKKLHKK | (SEQ ID NO: 37) |
| HA2-C6 | GLFGAIAGFIENGWEGMIDGRLLRL LLRLWRRLLRLLR | (SEQ ID NO: 38) |
| HA2-PK | GLFGAIAGFIENGWEGMIDGWYGPK KKRKV | (SEQ ID NO: 39) |

This group comprises additional W and H amino acids which may increase the affinity of peptides with cell membranes and increase endosomal escape. Also the n-terminal domain was replaced with GLW, which is reported to be important in CADY [Karidia, et al. 2009] and MPG [Simeoni, et al. 2003] peptides.

HA2, GLFGAIAGFIENGWEGMIDGWYG, has been added to facilitate the endosomal escape for some CPPs, e.g., Penetratin and HA2-Penetratin, and was proved to increase the transfection efficiency of penetratin. Moreover, an added nuclear localization sequence (NLS), PKKKRKV with lysine-rich segments, has shown high nuclear and cytoplasmic localization properties [Simeoni, et al. 2003].

VIII: Stearic Acid (STR) Modified Peptides

In another embodiment, the presently disclosed and/or claimed inventive concept(s) provides peptides having the following amino acid sequences:

TABLE 8

STR modified peptide sequences

| Name | Sequence | SEQ ID NO: |
|---|---|---|
| STR-C1 | CH3(CH2)16-GGGPKPKRKV | (SEQ ID NO: 40) |
| STR-HK | CH3(CH2)16-HHHPKPKRKV | (SEQ ID NO: 41) |
| STR-HKC | CH3(CH2)16-HHHCPKKKRKVC | (SEQ ID NO: 42) |

Stearic acid is one of the fatty acids occurring abundantly in the body and has high interaction ability with the cell membrane. It has been reported that the cell penetrating peptides with stearic acid modification at the N-terminal could increase the cellular uptake of siRNA-peptide complex [Tanaka, et al. 2010], which may be due to the increased affinity to the cell membrane mediated by stearic acid. Meanwhile, it is believed that stearic acid modified PEI could increase siRNA protection from degradation in Fetal Bovine Serum (FBS) as compared to the parent PEI [Alshamsan, et al. 2009].

In view of these reports, stearic acid was incorporated into the C1 family peptides to increase the membrane affinity of the hydrophobic domain and to enhance siRNA stability in serum. As in C1 family peptides the hydrophobic segments are separated from hydrophilic parts, it is easier to replace the hydrophobic domain with stearic acid to evaluate the effect of different hydrophobic segments. Three peptides were chosen from C1 family with different degree of hydrophobic interaction with cell membrane, and modified with stearic acid.

Meanwhile, the linker GGG was changed in STR-HK and STR-HKC to HHH to enhance the endosomal escape of the complex, as it is protonated at low pH and also to evaluate the effect of a different linker.

IX. Cysteamide (CYSt) Modified Peptides

In another embodiment, the presently disclosed and/or claimed inventive concept(s) provides peptides having one of the following amino acid sequences:

TABLE 9

CYSt modified peptide sequences

| Name | Sequence | SEQ ID NO: |
|---|---|---|
| C6-CYSt | RLLRLLLRLWRRLLRLLR-Cysteamide | (SEQ ID NO: 43) |
| C6M1-CYSt | RLWRLLWRLWRRLWRLLR-Cysteamide | (SEQ ID NO: 44) |
| C6M3-CYSt | RLWHLLWRLWRRLHRLLR-Cysteamide | (SEQ ID NO: 45) |
| C6M6-CYSt | GLWHLLLHLWRRLLRLLR-Cysteamide | (SEQ ID NO: 46) |

This group of peptides was modified with cysteamide group at the C-terminal. Cysteamide is the simplest stable aminothiol and a degradation product of amino acid cysteine. It has been reported that attaching cysteamide group at the C-terminus of peptide could promote efficient transfection of DNA-peptide complexes [Simeoni, et al. 2003]. It has also been studied that peptides modified with cysteamide at C-terminus shows higher potency to cross cell membranes than the original peptide [Crombez, et al. 2009].

This hypothesis has been extended to siRNA-peptide delivery system. To investigate the effect of cysteamide group in enhancing the transfection efficiency of complexes, peptides from C6 family with different levels of transfection efficiency were chosen and modified with cysteamide group at C-terminal.

Example 1

Peptide-siRNA Assemblies/Nanoparticles: Preparation and Transfection In Vitro

The ability of promising peptides to deliver siRNA was evaluated on CHO cells using GAPDH as the target gene. Chinese hamster ovary cells CHO-K1 (ATCC CCL-61) were derived as a subclone from the parental CHO cell line initiated from a biopsy of an ovary of an adult Chinese hamster. Glyceraldehyde-3-phosphate dehydrogenase (GAPDH) is a housekeeping gene widely expressed in diverse tissues and cell types and functions in a variety of cellular processes. The corresponding siRNA, i.e. Silencer® GAPDH siRNA (Human, Mouse, Rat), was purchased from Ambion. The molar concentration of siRNA was determined by absorption spectroscopy, using an extinction coefficient of 385103 L/mol cm.

A peptide array consisting of crude peptides with N-terminal acetylation and C-terminal amidation was purchased from Pepscan Systems (Leystad, Netherlands).

Formulation Protocol:

siRNA concentrations of 50 nM and Peptide/siRNA molar ratios of 20/1 and 40/1 were used in screening experiments.

Transfection Protocol

The cells were seeded with a confluency of 35,000 cells/well in F12K medium with 10% FBS without antibacterial agents, 24 hrs before transfection.

On the next day, rinse the cells with PBS buffer before transfection and add 200 µL of Opti-MEM. 100 µL of the complex solution (negative control siRNA-peptide and GAPDH siRNA-peptide) were added to each well.

The cells were incubated with the complex at 37° C. in an incubator. After 4 hours, 300 µL F12-K with 20% FBS was added without removing the transfection mixture.

The cells were rinsed and lysed 48 hours after the start of transfection.

Real-time RT-PCR is at present the most sensitive method for the detection of low abundance mRNA. Total RNA from the cells was extracted with TRIzol reagent (Invitrogen, Carlsbad, Calif., USA), then treated with chloroform (Sigma, Oakville, Ontario, Canada) and 2-propanol (Sigma, Oakville, Ontario, Canada) as recommended by the manufacturer. The RNA concentrations were measured by Nanodrop (Nanodrop spectrophotometer ND-1000, Thermo scientific, Ottawa, Canada). All the RNAs were reverse transcribed with Bio-Rad iScript cDNA synthesis kit according to the protocol. The cDNA synthesis was primed with a unique blend of oligo (dT) and random primers. PCR was performed with primers for mouse GAPDH gene with: 5'-TTGCTGTTGAAGTCGCAGGAG-3' (Primer 1, SEQ ID NO: 47) and 5'-TGTGTCCGTCGTGGATCTGA-3' (Primer 2, SEQ ID NO: 48) (Sigma, Oakville, Ontario, Canada). To avoid bias, real-time RT-PCR is usually referred to one or several internal control genes, which should not fluctuate during treatments [Nicot, et al. 2005]. Here, the house keeping gene cyclophilin was chosen as an internal control to normalize GAPDH gene. Normalization was performed by the amplification of mouse/rat cyclophilin mRNA with the following primers 5'-AGGGTTTCTCCACTTCGATCT-TGC-3' (Primer 3, SEQ ID NO: 49) and 5'-AGATG-GCACAGGAGGAAAGAGC AT-3' (Primer 4, SEQ ID NO: 50) (Sigma, Oakville, Ontario, Canada).

Figure 2:
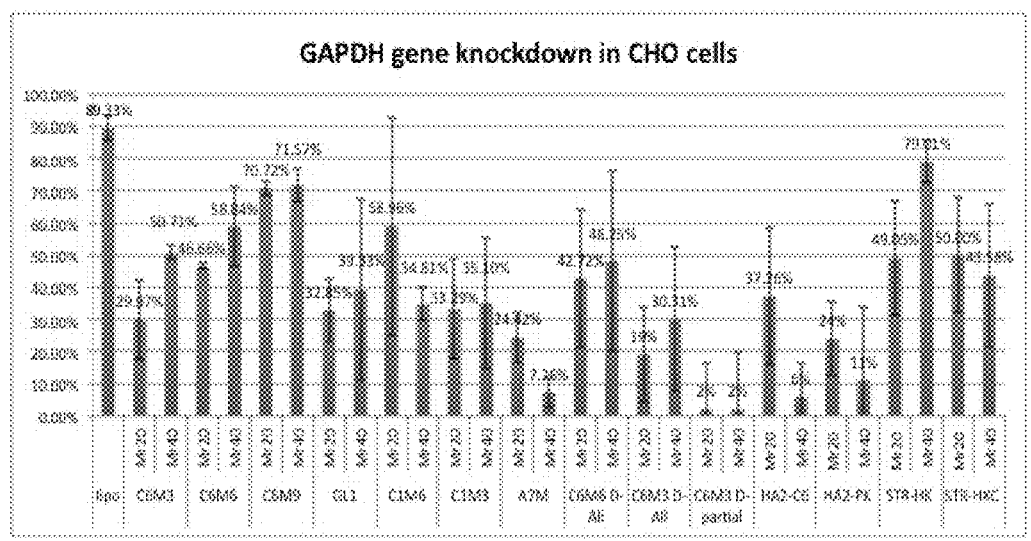
FIG. 2 illustrates intracellular silencing of GAPDH gene in CHO cells.

RT-PCR results of GAPDH siRNA complexed with different peptides at molar ratio 20 and 40 are shown in FIG. 2. FIG. 2 shows the intracellular silencing of GAPDH gene in CHO cells where siRNA were complexed with peptides at a molar ratio of 20:1 and 40:1. mRNA levels were measured 48 hours after transfection. The results shown in FIG. 2 correspond to an average of at least three separate experiments.

Example 2: Formulation Protocol can Refer to the Above Example

Transfection Protocol

For CHO-K1 cell line, 96-well plate and serum-free treatment:

The cells were seeded with a confluency of 5000 cells/well in F12K medium with 10% FBS without antibacterial agents, 24 hrs before transfection. The confluency of the cells was 40-60% the day of transfection.

The cells were rinsed with PBS and 50 uL of Opti-MEM was added, then 50 uL of the complex solution (siRNA-peptide or controls) was added to each well.

The cells were incubated with the complex at 37° C. in a CO2 incubator for 3-6 hours; a period of 4 hours is usually enough. After incubation, 50 uL F12K medium with 30% FBS was added without removing the transfection mixture.

The cells were rinsed and lysed 48 hours after the start of transfection.

GAPDH KDalert kit was used to measure the activity of enzymatic activity of glyceralde-hyde-3-phosphate dehydrogenase (GAPDH) in treated and control cells:

The KDalert™ GAPDH Assay Kit is a rapid, convenient, fluorescence-based method for measuring the enzymatic activity of glyceralde-hyde-3-phosphate dehydrogenase (GAPDH) in cultured cells derived from human, mouse, and rat. The KDalert GAPDH Assay Kit is designed to facilitate identification of optimal siRNA delivery conditions by assessment of GAPDH expression and knockdown at the protein level.

GAPDH is a tetrameric enzyme, composed of 36 kD protein subunits. It catalyzes the oxidative phosphorylation of glyceraldehyde-3-phosphate (G-3-P) to bisphosphoglycerate (BPG):

The KDalert GAPDH Assay measures the conversion of NAD+ to NADH by GAPDH in the presence of phosphate and G-3-P. Under the recommended assay conditions, the rate of NADH production is proportional to the amount of GAPDH enzyme present. Thus the assay can be used to accurately determine the amount of GAPDH protein in a sample.

Experimental Results

Figure 3A:
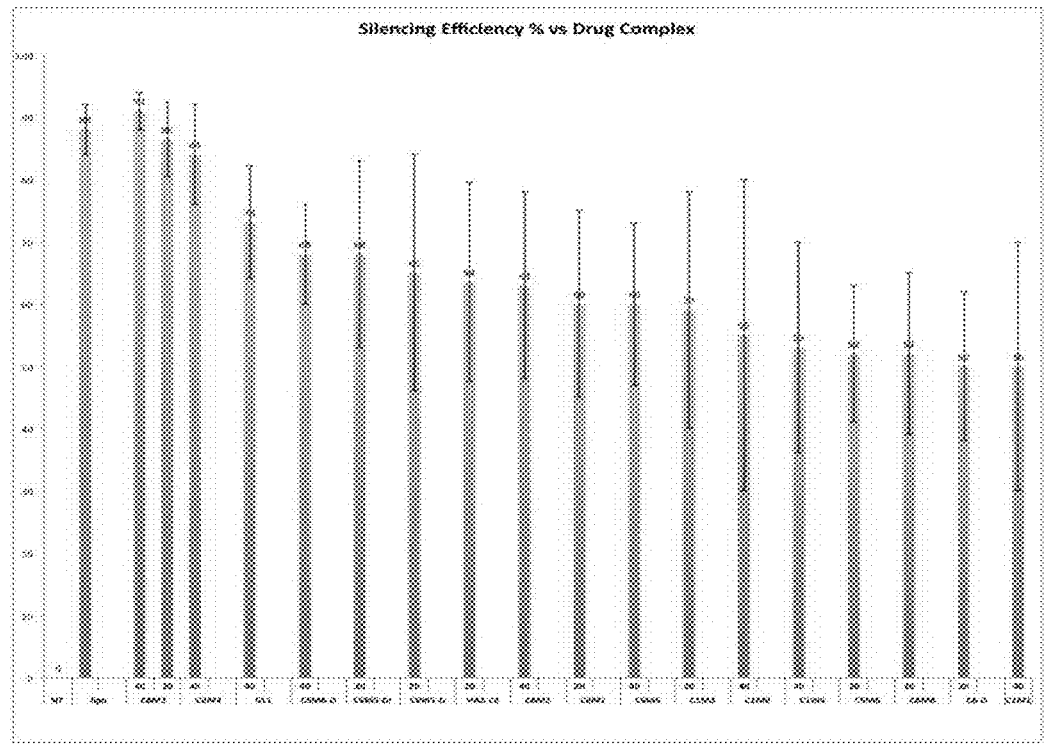
FIGS. 3A and 3B illustrate silencing efficiency of peptides-siRNA complex, with two Molar Ratios: 20 and 40.
Figure 3B:
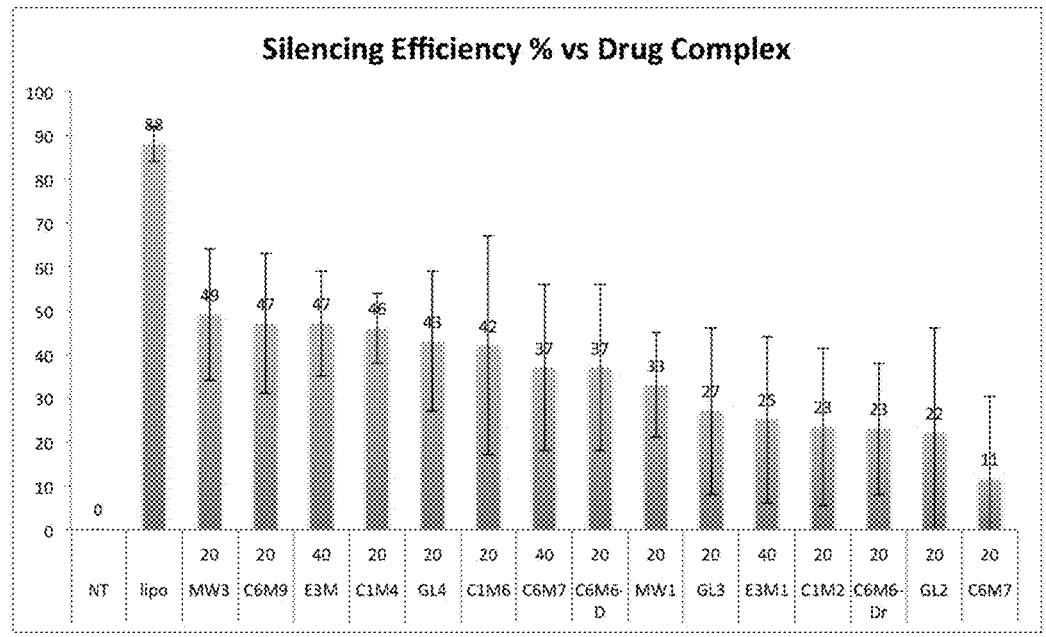
Figure 4A:
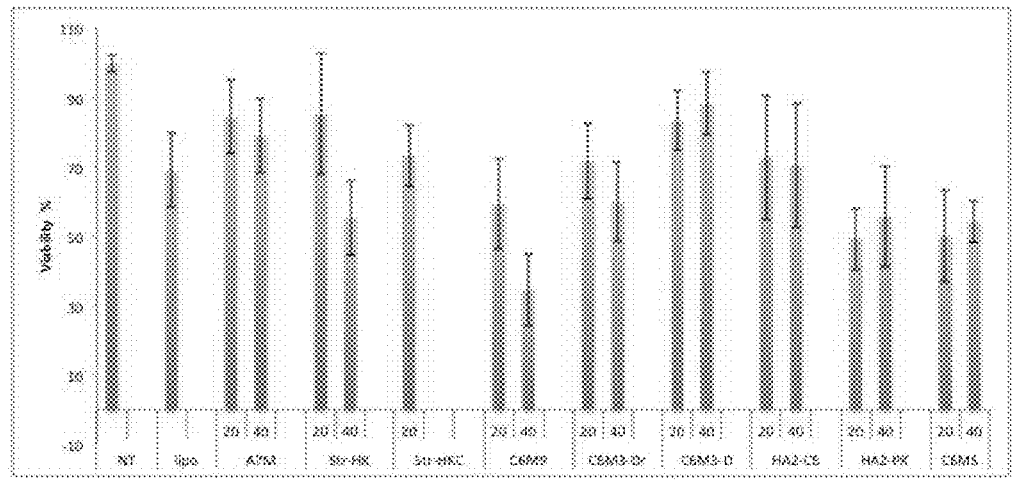
FIGS. 4A and 4B illustrate the cytotoxicity of peptide-siRNA complexes against CHO-K1 cells.
Figure 4B:
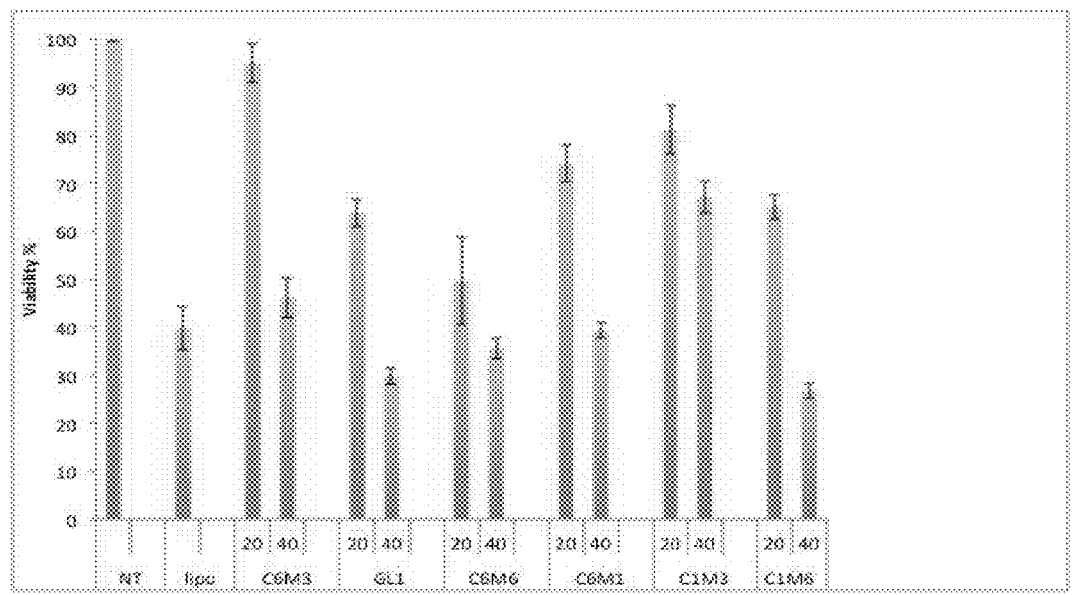

FIG. 3A shows the silencing efficiency of peptides-siRNA complex, with two Molar Ratio: 20 and 40. FIG. 3B shows the results of a different run for the silencing efficiency of peptides-siRNA complex, with the same Molar Ratios. FIG. 4A shows the cytotoxicity of 18 peptide-siRNA complexes against CHO-K1 cells. FIG. 4B shows the cytotoxicity of 6 peptide-siRNA complexes against CHO-K1 cells.

Example 3: Size of the Peptide-siRNA Complexes

Figure 5:
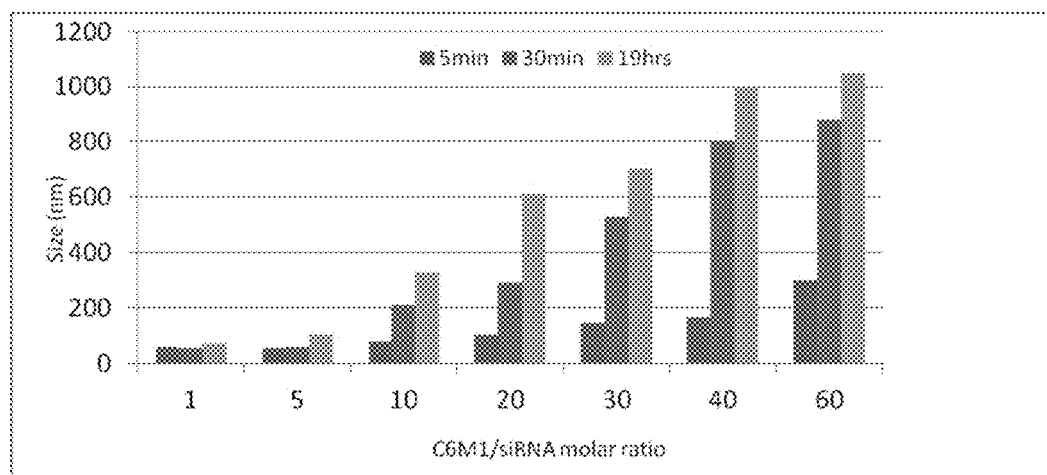
FIG. 5 illustrates the size of the C6M1-siRNA complex in PBS over time.

Dynamic Light Scattering (DLS) method was applied to measure the size of the complex in Zeta Sizer Nano Series (Malvern). FIG. 5 shows the size of the complexes of C6M1 peptide and siRNA at peptide/siRNA molar ratios from 1:1 to 60:1 over time. As shown, the size of the complex increases over time, by increasing peptide/siRNA molar ratio. As the size range of 100 to 250 nm might be the appropriate range for in vitro and in vivo treatment, the molar ratio of 20:1 with an incubation time of less than 30 min might be the optimum conditions for complex preparation.

Example 4: Fluorescence Spectroscopy

Figure 6:
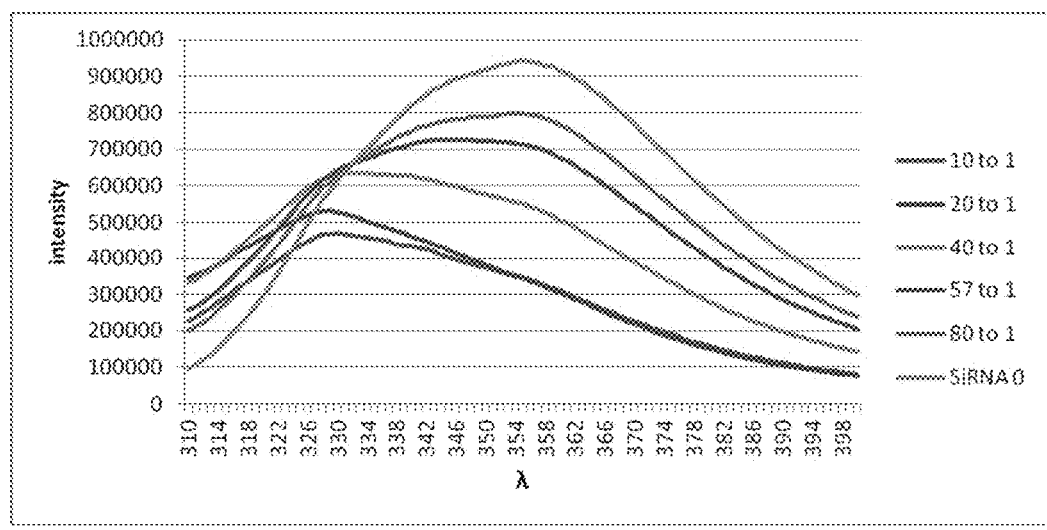
FIG. 6 illustrates fluorescence spectroscopy results of C6M1-siRNA complexes at different molar ratios with a fixed concentration of C6M1.

The peptide C6M1 was used in this experiment to study the interaction between peptide and siRNA using fluorescence spectroscopy method. C6M1 has four tryptophan amino acids which can be used as fluorescence probe. As shown in FIG. 6, by adding more siRNA to samples of fixed C6M1 concentration, the intensity of fluorescence decreased, indicating the interaction between peptide and siRNA. A blue shift from 355 to 330 nm was also observed in molar ratios of less than 40:1, clearly at 20:1 and 10:1, probably due to the change in the environment of tryptophan by adding more hydrophilic siRNA molecules.

Figure 7:
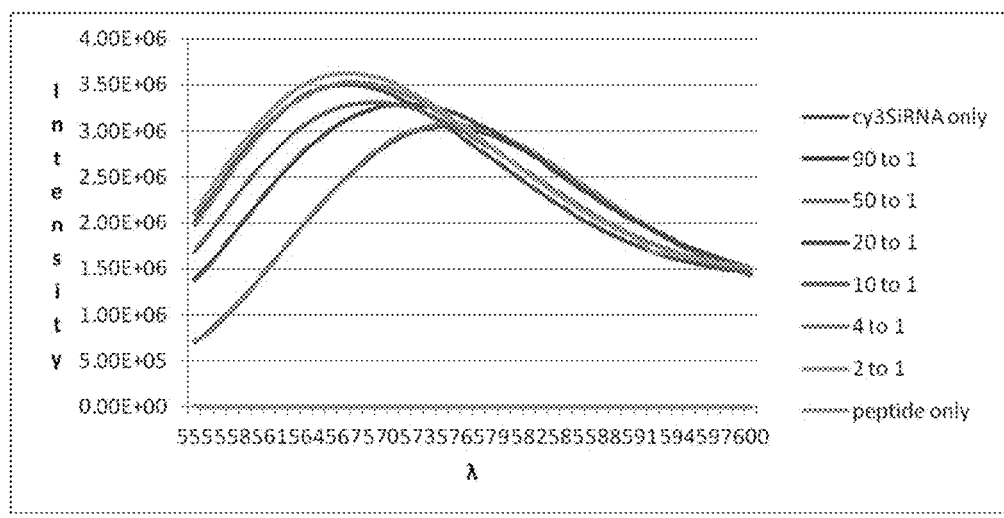
FIG. 7 illustrates fluorescence spectroscopy results of C6M1 and labelled siRNA complexes at different molar ratios with a fixed concentration of C6M1.

A similar experiment was also performed by tracking the fluorescence property of labeled siRNA, interacting with C6M1. As shown in FIG. 7, no significant change in the fluoresce spectra of siRNA was observed at low molar ratios of 2:1 and 4:1. However by adding more peptides, the intensity decreased at molar ratios of 10:1 and 20:1, indicating the interaction and enclosing the siRNA by peptide molecules. The red shift could also be an indicator of a change in the siRNA environment and/or conformational change in siRNA structure upon interacting with peptides.

Example 5: C6M1/siRNA Complex Inhibits Proliferation of Cancer Cells in Nude Mice The potency of C6M1/siRNA complexes to inhibit cancer cell proliferation was investigated on a tumor animal model. siRNA targeting the bcl-2 gene product was used here. The bcl-2 protein regulates the mitochondria-mediated apoptosis pathway, and various cell death stimuli, including chemotherapeutic agents. So that a drug to reduce the levels of this protein would be expected to promote apoptosis and would therefore be considered a promising therapeutic agent.

The animal model was established by subcutaneous inoculation of 5×106 A549 cells in BALB/c nude mice at the right armpit. When the tumor volume reached 100-200 mm3, the complexes were injected. The C6M1/siRNA complexes were prepared as described before and injected directly into the tumor. Treatments were given every 3 days, for a total of nine treatments at the dose of 4 μg siRNA per mouse. The body weight and tumor diameters were measured everyday. The tumor volume was calculated as follows:

Tumor volume=0.5×(width)2×length.        1.

Mice were killed on the 27th day after first injection. Results corresponding to the average of two different animals.

Figure 8A:
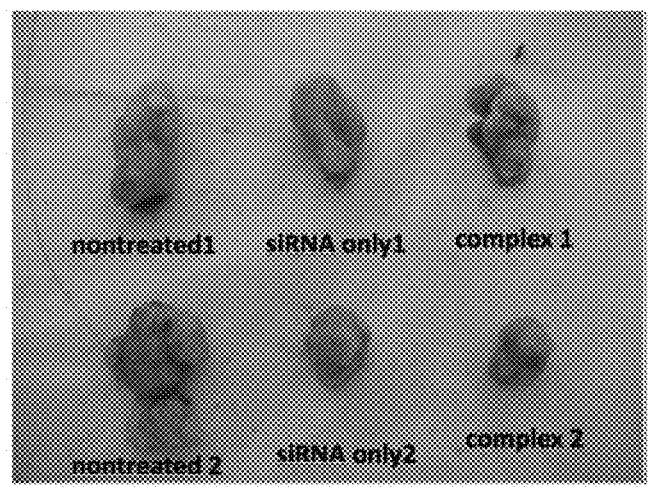
FIGS. 8A, 8B, and 8C illustrate in vivo results.
Figure 8B:
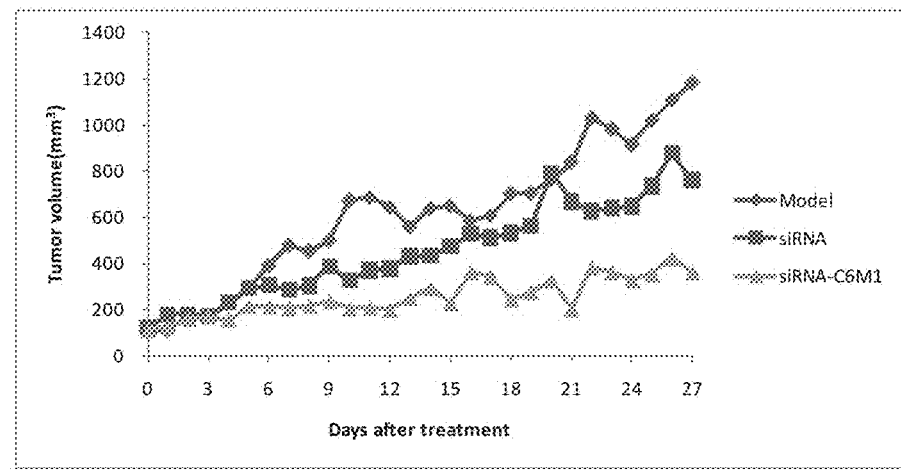
Figure 8C:
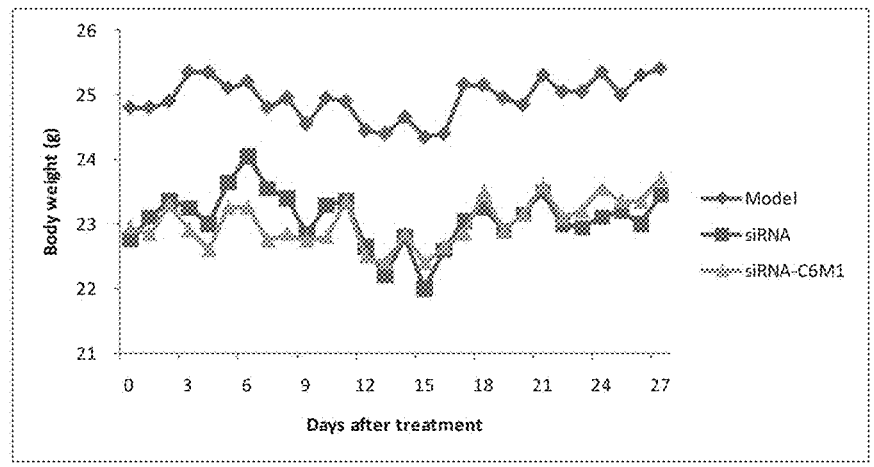

The results are shown in FIGS. 8A-C. These results suggested that bcl-2 siRNA complexed with peptide C6M1 specifically inhibits tumor growth, as a significant reduction in the tumor size was observed after the treatment. Moreover, the complexes showed low toxic effect. During treatment, if the average weight of mice in treated group (tumor tissue exclusive) have decreased (self-control) by more than 15%, it indicates that the drug has toxicity reaction, then the dosage should be reduced to re-test. In our experiment, the body weight of six mice in each group did not change significantly during the treatment. All these results demonstrate that C6M1 is an effective and safe tool for in vivo siRNA delivery.

Mice were killed by dislocation, separate tumor and weighed it. We calculated average weight of each group and tumor inhibition rate. The siRNA group inhibition rate is 37%, siRNA-C6M1 53%, which can inhibit tumor growth significantly.

Although the presently disclosed and/or claimed inventive concept(s) has been described with reference to certain specific embodiments, various modifications thereof will be apparent to those skilled in the art without departing from the purpose and scope of the presently disclosed and/or claimed inventive concept(s) as outlined in the claims appended hereto. Any examples provided herein are included solely for the purpose of illustrating the presently disclosed and/or claimed inventive concept(s) and are not intended to limit the presently disclosed and/or claimed inventive concept(s) in any way. Any drawings provided herein are solely for the purpose of illustrating various aspects of the presently disclosed and/or claimed inventive concept(s) and are not intended to be drawn to scale or to limit the presently disclosed and/or claimed inventive concept(s) in any way. The disclosures of all prior art recited herein are incorporated herein by reference in their entirety.

REFERENCES

Alshamsan, A., Haddadi, A., Incani, V., Samuel, J., Lavasanifar, A., Uludag, H. (2009). Formulation and delivery of siRNA by oleic acid and stearic acid modified polyethylenimine. Molecular Pharmacology, 6, 121-133.
Benoit, J., Vonarbourg, A., Passirani, C., Saulnier, P. Parameters influencing the stealthiness of colloidal drug delivery systems. (2006). Biomaterials, 27, 4356-4373.
Biverståhl, H., Andersson, A., Gräslund, A., & Mäler, L. (2004). NMR solution structure and membrane interaction of the N-terminal sequence (1-30) of the bovine prion protein. Biochemistry, 47, 14940-14947.
Cartier, R., Reszka, R. Utilization of synthetic peptides containing nuclear localization signals for nonviral gene transfer systems. (2002). Gene therapy, 9, 157-167.
Chen, P., Jafari, M., Jiang, J., Fung, S.-yu, & Yang, H. (2011). (WO/2011/020188) PEPTIDE SEQUENCES AND PEPTIDE-MEDIATED SIRNA DELIVERY.
Chou, P. Y., Fasman, G. D. (1973) Structural and functional role of leucine residues in proteins. Journal of Molecular Biology, 74, 263-281.
Crombez, L., Aldrian-herrada, G., Konate, K., Nguyen, Q. N., McMaster, G. K., Brasseur, R., Heitz, F., Divita, G. (2009). A new potent secondary amphipathic cell-penetrating peptide for siRNA delivery into mammalian cells. Molecular Therapy, 17, 95-103.
Daniel Knappe. et al. (2011) Bactericidal oncocin derivatives with superior stabilities. International Journal of Antimicrobial Agents, 37, 166-170.
Derossi, D., Joliot, a H., Chassaing, G., & Prochiantz, a. (1994). The third helix of the Antennapedia homeodomain translocates through biological membranes. The Journal of biological chemistry, 14, 10444-10450.
Deshayes, S., Heitz, A., Morris, M. C., Charnet, P., Divita, G., & Heitz, F. (2004). Insight into the mechanism of internalization of the cell-penetrating carrier peptide Pep-1 through conformational analysis. Biochemistry, 6, 1449-1457.
Deshayes, S., Plenat, T., Aldrian-Herrada, G., Divita, G., Grimmellec, C. D., Heitz, F. (2004). Primary amphipathic cell-penetrating peptides: structural requirements and interactions with model membranes. Biochemistry, 43, 7698-7706.
Endoh, T., Ohtsuki, T. (2009). Cellular siRNA delivery using cell-penetrating peptides modified for endosomal escape. Advanced drug delivery reviews, 9, 704-709.
Engelke, D. R. R., Rossi, J. J. RNA interference; Methods in enzymology. (2005). 6876-6879, v. 39; Elsevier Academic Press: San Diego.
Fire, A., Xu, S. Q., Montgomery, M. K., Kostas, S. A., Driver, S. E., Mello, C. C. Potent and specific genetic interference by double-stranded RNA in Caenorhabditis elegans. (1998). Nature, 391, 806-811.
Futaki, S., Suzuki, T., Ohashi, W., Yagami, T., Tanaka, S., Ueda, K., et al. (2001). Arginine-rich peptides. An abundant source of membrane-permeable peptides having potential as carriers for intracellular protein delivery. The Journal of biological chemistry, 8, 5836-40.
Jarvert, P., Langel, K., El-Andaloussi, S., Langel, U. Applications of cell-penetrating peptides in regulation of gene expression. (2007). Biochemical Society Transection, 35, 770-774.
Karidia, K. et al. Insight into the cellular uptake mechanisms of a secondary amphipathic cell-penetrating peptide for siRNA delivery. Biochemistry, 2010, 49, 3393-3402.
Knappe, D., Kabankov, N., Hoffmann, R. Bactericidal oncocin derivatives with superior stabilities. (2011). International Journal of Antimicrobial Agents, 37. 166-170.
Langel Ü. Handbook of cell-penetrating peptides, 2nd ed.; Boca Raton: Taylor & Francis, 2007.
Mahato, R. I. Biomaterials for delivery and targeting of proteins and nucleic acids; CRC Press: Boca Raton, 2005.
Lo, S. L., Wang, S. An endosomolytic Tat peptide produced by incorporation of histidine and cysteine residues as a nonviral vector for DNA transfection. (2008). Biomaterials, 15, 2408-2414.
Manoharan, M. RNA interference and chemically modified small interfering RNAs. (2004). Current Opinion Chemical Biology, 8, 570-579.
Moghimi, S. M., Bonnemain, B. Subcutaneous and intravenous delivery of diagnostic agents to the lymphatic system: applications in lymphoscintigraphy and indirect lymphography. (1999). Advanced Drug Delivery Reviews, 37, 295-312.

Mok, H., Park, T. G. Self-crosslinked and reducible fusogenic peptides for intracellular delivery of siRNA. (2008). Biopolymers, 89, 881-888.

Nicot, N., Hausman, J. F., Hoffmann, L, Evers, D. House-keeping gene selection for real-time RT-PCR normalization in potato during biotic and abiotic stress. (2005). Journal of experimental botany, 56, 2907-2914.

Novina, C. D., Sharp, P. A. The RNAi revolution. (2004). Nature, 430, 161-164.

Oehlke, J., Scheller, A., Wiesner, B., Krause, E., Beyermann, M., Klauschenz, E., Melzig, M., Bienert, M. Cellular uptake of an α-helical amphipathic model peptide with the potential to deliver polar compounds into the cell interior non-endocytically. (1998). Biochimica et Biophysica Acta/Biomembranes, 1414, 127-139.

Oliveira, S., Storm, G., Schiffelers, R. M. Targeted delivery of siRNA. (2006). Jounal of Biomedicine and Biotechnology, 1-9.

Paddison, P. J., Vogt, P. K. K. RNA interference; Current topics in microbiology and immunology; v. 32; Springer: Berlin.

Simeoni, F., Morris, M. C., Heitz, F., Divita, G. Insight into the mechanism of the peptide-based gene delivery system MPG: implications for delivery of siRNA into mammalian cells. (2003). Nucleic Acids Research, 31, 2717-2724.

Tanaka, K., Kanazawa, T., Ogawa, T., Takashima, Y., Fukuda, T., Okada, K. Disulfide crosslinked stearoyl carrier peptides containing arginine and histidine enhance siRNA uptake and gene silencing. (2010). International Journal of Pharmaceutics, 398, 219-224.

Verma, S., Jager, S., Thum, O., Famulok, M. Functional tuning of nucleic acids by chemical modifications: Tailored oligonucleotides as drugs, devices and diagnostics. (2003). The Chemical Record, 3, 51-60.

Wadia, J. S., Schaller, M., Williamson, R. A., & Dowdy, S. F. (2008). Pathologic prion protein infects cells by lipid-raft dependent macropinocytosis. PloS one, 3, e3314.

Wang, Y. H., Chen, C. P., Chan, M. H., Chang, M., Hou, Y. W., Chen, H. H. Arginine-rich intracellular delivery peptides noncovalently transport protein into living cells. (2006). Biochemical and biophysical research communications, 3, 758-767.

Vives, E. Present and future of cell-penetrating peptide mediated delivery systems: "Is the Trojan horse too wild to go only to Troy?". (2005). Journal of Controlled Release, 109, 77-85.

Zhang, N. Y., Du, Q., Wahlestedt, C., Liang, Z. C. RNA interference with chemically modified siRNA. (2006). Current Topics Medicinal Chemistry, 6, 893-900.

What is claimed is:

1. A complex comprising:
   a peptide having the amino acid sequence according to SEQ ID NO: 41 or 42; and
   a cargo molecule.

2. The complex according to claim 1, wherein the cargo molecule is a nucleic acid.

3. The complex according to claim 2, wherein the nucleic acid is short interfering RNA (siRNA).

4. The complex of claim 3, wherein the siRNA is complexed with the peptide at a molar ratio within the range of 1:1 to 60:1.

5. The complex of claim 3, wherein the siRNA is complexed with the peptide at a molar ratio within the range of 5:1 to 60:1.

6. The complex of claim 3, wherein the siRNA is complexed with the peptide at a molar ratio of 20:1.

7. The complex of claim 3, wherein the siRNA is complexed with the peptide at a molar ratio of 40:1.

8. A pharmaceutical composition comprising a complex according to claim 3 for delivering a therapeutically effective amount of siRNA.

9. The pharmaceutical composition of claim 8, wherein the siRNA is complexed with the peptide at a molar ratio within the range of 1:1 to 60:1.

10. A method of reducing the levels of a gene product within a cell or tissue of an animal comprising:
    administering the pharmaceutical composition of claim 8.

11. The method of claim 10, wherein the cell is a tumor cell or the tissue is tumor tissue.

12. The method of claim 10, wherein the siRNA targets a gene product that regulates apoptosis.

13. The method of claim 12, wherein the gene that regulates apoptosis is bcl-2.

14. The method of claim 10, wherein the siRNA is complexed with the peptide at a molar ratio within the range of 1:1 to 60:1.

15. A method of delivering siRNA into a cell, comprising:
    administering the complex of claim 3 to the cell.

16. The method of claim 15, wherein the cell is a CHO cell.

17. The method of claim 15, wherein the siRNA reduces the levels of an endogenous protein of the cell.

18. The method of claim 15, wherein the siRNA is complexed with the peptide at a molar ratio within the range of 1:1 to 60:1.

* * * * *

UNITED STATES PATENT AND TRADEMARK OFFICE
CERTIFICATE OF CORRECTION

PATENT NO. : 9,950,073 B2  
APPLICATION NO. : 15/407802  
DATED : April 24, 2018  
INVENTOR(S) : Pu Chen et al.

Page 1 of 1

It is certified that error appears in the above-identified patent and that said Letters Patent is hereby corrected as shown below:

In the Specification  
Column 16, Line 25: After "Zhang," delete "N.Y.," and replace with -- H.Y., --

Signed and Sealed this  
Fifth Day of June, 2018

Andrei Iancu  
*Director of the United States Patent and Trademark Office*